United States Patent [19]

Bekiarian et al.

[11] Patent Number: 5,382,718
[45] Date of Patent: Jan. 17, 1995

[54] CYCLOFLUOROALKYLATED FULLERENE COMPOUNDS

[75] Inventors: Paul G. Bekiarian; Paul J. Fagan; Paul J. Krusic, all of Wilmington, Del.

[73] Assignee: E. I. Du Pont de Nemours and Company, Wilmington, Del.

[21] Appl. No.: 122,118

[22] Filed: Sep. 16, 1993

[51] Int. Cl.$^6$ .................... C07C 17/24; C07C 17/28; C07C 17/32; C07C 22/08

[52] U.S. Cl. .................... 570/129; 558/388; 500/80; 500/102; 562/826; 562/840; 562/849; 562/850; 562/853; 568/660; 568/661; 570/143; 570/144

[58] Field of Search .................... 570/129; 558/388; 560/80, 102; 562/826, 840, 849, 850, 853; 568/660, 661

[56] References Cited

PUBLICATIONS

A. Rao et al., *Science*, 259:955–957 (Feb. 12, 1993).
S. Hoke et al., *J. Org. Chem.*, 57:5069–5071 (1992).
S. Njima, *Nature*, 354:56–58 (Nov. 7, 1991).
M. Tsuda et al., *Chem. Soc. Jap. Chem. Lett.* pp. 2333–2334 (1992).
M. Prato, *J. Org. Chem.* 58:3613–3615 (1993).
M. Hudlicky, "Chemistry of Organic Fluorine Compounds", 2 Ed., pp. 450–463 (1976).
W. Kratschmer et al., *Articles,* 347:354–358 (Sep. 27, 1990).
F. Diederrich et al., *Science*, 252:548–551 (Apr. 26, 1991).
C. Smart et al., *Chem. Phys. Lett.*, 188(3,4):171–176 (Jan. 10, 1992).
P. Krusic et al., *Science*, 254:1183–1185 (Nov. 22, 1991).

*Primary Examiner*—Joseph E. Evans

[57] ABSTRACT

Mixtures of cyclofluoroalkylated fullerenes are provided by the thermal 2+2 cycloaddition of fluoroalkenes to a solution or slurry of a fullerene. The cyclofluoroalkylated fullerene mixtures are useful as lubricants or additives to lubricants; in fluorocarbon and/or chlorofluorocarbon based cooling systems; in adhesives for fluorocarbon based polymers and in gas separation membranes.

7 Claims, No Drawings

CYCLOFLUOROALKYLATED FULLERENE COMPOUNDS

BACKGROUND OF THE INVENTION

This invention relates to reactions of fluoroalkenes with fullerenes, and the cyclofluoralkylated products derived from these reactions.

Recent success in synthesizing macroscopic quantities of carbon clusters such as $C_{60}$ and $C_{70}$ (known as fullerenes), by W. Kratschmer et al., Nature, 347–354 (1990), has opened the door to the study of this new class of organic compounds. Kratschmer et al. describe the fullerene molecule $C_{60}$ (also known as buckminsterfullerene) as a centrosymmetric truncated icosahedron. Pure solid buckminsterfullerene consists of a somewhat disordered face centered cubic or hexagonal close packing of the centrosymmetric molecules. Isolation and characterization of higher fullerenes, specifically $C_{76}$, $C_{84}$, $C_{90}$, and $C_{94}$, have been disclosed by Francois Diederich et al., Science, Vol. 252, pages 548–551 (1991). Mixtures of giant fullerene molecules, e.g., $C_{540}$, have been discussed by C. Smart et al., Chem. Phys. Lett., Vol. 188, No. 3,4, pages 171–176 (Jan. 10, 1992).

Fluorinated alkenes are known to undergo thermal cycloaddition with themselves and other alkenes to form fluorocyclobutane rings (Hudlicky, M., "Chemistry of Organic Fluorine Compounds, 2nd ed.", Ellis Hotwood Ltd., pp. 450–463, 1976). Buckminsterfullerene ($C_{60}$) has been proposed to undergo photochemical cycloaddition with itself in the solid state (Rao, A. M.; Zhou, Ping; Wang, Kai An; Hager, G. T.; Holden, J. M.; Wang, Ying; Lee, W. T.; Bi, Xian Xin; Eklund, P. C.; et al., Science, 1993, vol. 259. pp 955–7). Benzyne (generated as an intermediate in situ) is reported to add to $C_{60}$ (Tsuda, M.; Ishida, T.; Nogami, T.; Kurono, S.; Ohashi, M., Chem. Lett., 1992, No. 12, pp 2333–2334; Hoke, II S. H.; Molstad, J; Dilettato, D; Jay, M. J.; Carlson, Do; Kahr, B.; Cooks, R. G., J. Org. Chem., 1992, vol. 57, pp 5069–5071). Quadricyclane is reported to thermally add to $C_{60}$ (Prato, M., et al., J. Org. Chem., 1993, vol. 58, pp 3613–3615). There are no known examples of the thermal 2+2 cycloaddition of an alkene to $C_{60}$ or other fullerene in the literature.

Earlier filed, commonly assigned U.S. Pat. No. 08/021,395 discloses fluoroalkylated fullerene compounds.

An object of this invention is to provide a mixture comprising cyclofluoroalkylated fullerene compounds by reaction of fullerenes with fluoroalkenes.

SUMMARY OF THE INVENTION

This invention comprises a mixture of cyclofluoroalkylated fullerene compounds comprising formula (I)

$$(C_{60+2n})(CF_2CR^1R^2)_w R^3_x R^4_y R^5_z \qquad \text{I}$$

wherein:

$R^1$ and $R^2$ are independently H, F, Cl, Br, CN, a branched or straight chain alkyl, alkylether, alkoxy, alkoxyether, fluoro-alkyl, fluoroalkylether, fluoroalkoxy, fluoroalkoxyether, aryl, aryloxy, fluoro-aryl, or fluoroaryloxy group of from 1 to about 100 carbon atoms and 0 to 50 oxygen atoms; optionally substituted with at least one of the following class comprised of H, Cl, Br, carbinol, carboxylic acid ester, carboxylic acid halide, sulfonyl fluoride, carbonitrile;

$R^3$ is F or a branched or straight chain fluoroalkyl or fluoroalkylether group of from 1 to about 100 carbon atoms and 0 to 50 oxygen atoms;

$R^4$ is a branched or straight chain hydrocarbon alkyl or alkyl ether or aromatic hydrocarbon of from 1 to about 100 carbon atoms and 0 to 50 oxygen atoms;

$R^5$ is independently one or more selected from H, F and Cl;

n is an integer from 0 to about 470;

w is an integer from 1 to $16+(n/2)$ for n=an even integer, or from 1 to $16+((n+1)/2)$ for n=an odd integer;

x is an integer from 0 to about $24+n$;

y is an integer from 0 to about $24+n$;

z is an integer from 0 to about $35+n$.

This invention also comprises a thermolysis process for the preparation of a mixture comprising cyclofluoroalkylated fullerene compounds said process comprising thermolyzing a solution or slurry of fullerene compounds of formula (II)

$$(C_{60+2n}) R^3_x R^4_y R^5_z \qquad \text{(II)}$$

wherein:

$R^3$ is F or a branched or straight chain fluoroalkyl or fluoroalkylether group of from 1 to about 100 carbon atoms and 0 to 50 oxygen atoms;

$R^4$ is a branched or straight chain hydrocarbon alkyl or alkyl ether or aromatic hydrocarbon of from 1 to about 100 carbon atoms and 0 to 50 oxygen atoms;

$R^5$ is independently one or more selected from H, F and Cl;

n is an integer from 0 to about 470;

x is an integer from 0 to about $24+n$;

y is an integer from 0 to about $24+n$; and z is an integer from 0 to about $35+n$, with a fluoroalkene of formula (III)

$$CF_2CR^1R^2 \qquad \text{(III)}$$

wherein:

$R^1$ and $R^2$ are independently H, F, Cl, Br, CN, a branched or straight chain alkyl, alkylether, alkoxy, alkoxyether, fluoroalkyl, fluoroalkylether, fluoroalkoxy, fluoroalkoxyether, aryl, aryloxy, fluoroaryl, or fluoroaryloxy group of from 1 to about 100 carbon atoms and 0 to 50 oxygen atoms; optionally substituted with at least one of the following class comprised of H, Cl, Br, carbinol, carboxylic acid ester, carboxylic acid halide, sulfonyl fluoride, carbonitrile, to yield a mixture of cyclofluoroalkylated fullerene compounds comprising formula (I), $(C_{60+2n})(CF_2CR^1R^2)_w R^3_x R^4_y R^5_z$, as defined above.

In the mixture of cyclofluoroalkylated fullerene compounds of formula (I), $R^3$, $R^4$ and $R^5$ are each independently attached directly to the $C_{60+2n}$ molecules. The two carbon atoms of the group $(CF_2CR^1R^2)$ are each attached to the $C_{60+2n}$ molecule and to each other, forming what is known in this art as a 2+2 cyclo adduct.

The description of the claimed compounds as a "mixture" indicates that due to practical considerations and the present state of the art the starting fullerene compounds will most likely be comprised of a mixture of $C_{60}$ molecules together with $C_{60+2n}$ molecules, wherein n may be 0 to about 470, most likely n is 1 to 5.

Starting fullerene compounds of formula (II) substituted with $R^3$ $R^4$ and/or $R^5$ can also be comprised of a mixture. Not only can the fullerene compounds, to which the $R^3$, $R^4$ and/or $R^5$ molecules are attached, be a mixture of $C_{60}$ together with $C_{60+2n}$ molecules, but the individual $R^3$, $R^4$ and/or $R^5$ molecules attached to them may vary from compound to compound within the mixture in both the number of substituents per fullerene compound and structure. For example, a starting mixture may be comprised of fullerene compounds such as: $C_{60}R^3H$ together with $C_{60}(R^{3'})_2$ and $C_{70}(R^3)_2$, wherein $R^3$ and $R^{3'}$ are two different $R^3$ fluorocarbons. Thus, the reaction of these mixtures of fullerene molecules with the fluoroalkene reactants of the invention yields a mixture of product cyclofluoroalkylated fullerene molecules. Further, it is known that the fluoroalkene reactant molecules may add nonuniformly to the surface of each of the fullerene molecules within each reaction mixture. Because of this fact also, therefore, the claimed cyclofluoroalkylated fullerenes of the invention are most properly described herein as "mixtures."

DETAILED DESCRIPTION OF THE INVENTION

This invention provides a mixture of cyclofluoroalkylated fullerene compounds, preferably cycloperfluoroalkylated fullerene compounds, comprising formula (I)

$$(C_{60+2n})(CF_2CR^1R^2)_w R^3_x R^4_y R^5_z \qquad (I)$$

wherein:

$R^1$ and $R^2$ are independently H, F, Cl, Br, CN, a branched or straight chain alkyl, alkylether alkoxy, alkoxyether, fluoroalkyl, fluoroalkylether, fluoroalkoxy, fluoro-alkoxyether, aryl, aryloxy, fluoroaryl, fluoroaryloxy group of from 1 to about 100 carbon atoms and 0 to 50 oxygen atoms; optionally substituted with at least one of the following class comprised of H, Cl, Br, carbinol, carboxylic acid ester, carboxylic acid halide, sulfonyl fluoride, carbonitrile;

$R^3$ is F or a branched or straight chain fluoroalkyl or fluoroalkylether group, preferably perfluoralkyl or perfluoro-alkylether, of from 1 to about 100 carbon atoms and 0 to 50 oxygen atoms, preferably 1-12 carbon atoms and 0-6 oxygen atoms;

$R^4$ is a branched or straight chain hydrocarbon alkyl or alkyl ether or aromatic hydro-carbon of from 1 to about 100 carbon atoms and 0 to 50 oxygen atoms, preferably 1-12 carbon atoms and 0-6 oxygen atoms;

$R^5$ is independently one or more selected from H, F and Cl, preferably H;

n is an integer from 0 to about 470, preferably an integer from 0 to about 200 and, most preferably, an integer from 0 to about 5;

w is an integer from 1 to $16+(n/2)$ for n=an even integer, or from 1 to $16+((n+1)/2)$ for n=an odd integer;

x is an integer from 0 to about 24+n, preferably an integer from 0 to about 3+n;

y is an integer from 0 to about 24+n, preferably an integer from 0 to about 3+n;

z is an integer from 0 to about 35+n.

The compound is exemplified below, wherein in Formula I $(C_{60+2n})(CF_2R^1R^2)_w R^3_x R^4_y R^5_z$; n is 0, $R^1$ and $R^2$ are F, and x, y and z are 0.

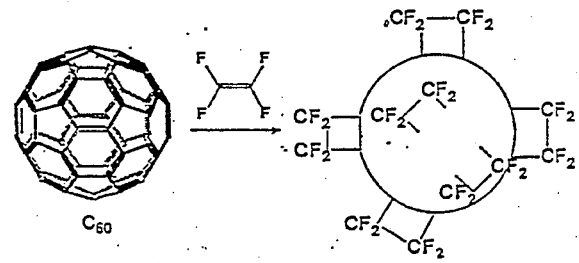

It is contemplated by the present inventors that carbon nanotubules as first prepared by Iijima (S. Iijima, Nature, Vol. 354, pp. 56–58 (1991) will also react and be cyclofluoroalkylated by the procedures described in this invention. This is based on the structural similarity of the endcaps of these tubes to fullerenes and the curved nature of the tubule surfaces which is characteristic of fullerenes such as $C_{60}$ and $C_{70}$.

The thermolysis process for cycloaddition of fluoroalkenes with themselves and other alkenes to form fluorocyclobutane rings is generally known in the art, for example Hudlicky, M., "Chemistry of Organic Fluorine Compounds, 2nd ed" Ellis Horwood Ltd, pp 450–463, 1976. The thermolysis process to prepare the mixtures of cyclofluoroalkylated fullerene compounds of formula (I) $(C_{60+2n})(CF_2CR^1R^2)_w R^3_x R^4_y R^5_z$, in accordance with this invention comprises heating fullerene compounds of formula (II) $(C_{60+2n})R^3_x R^4_y R^5_z$, with fluoroalkene compounds of formula (III), $CF_2CR^1R^2$, either as pure fluoroalkenes (e.g., tetrafluoroethylene) or as mixtures of fluoroalkenes, from about 100° to about 350° C. preferably from about 150° to about 250° C., and most preferably from about 150° to about 200° C. without, or preferably with, an organic or halocarbon solvent, such as 1,2,4-trichlorobenzene, under a pressure of about 0 to about $1.1 \times 10^7$ Pascals (0 to about 1600 psi) of the fluoroalkene, from about 1 hour to about 96 hours, preferably about 1 hour to about 18 hours. Typically the reaction is carried out in a sealed stainless steel pressure vessel, with a pressure gauge for determining the pressure, and an internal thermocouple for measuring temperature.

The product from the above reactions is generally isolated by first evaporating or distilling off under reduced pressure all or most of the excess compounds of formula (III), $CF_2CR^1R^2$ and any solvent. The product is redissolved in an organic or halocarbon solvent such as tetrahydrofuran, 1,1,2-trichlorotrifluoroethane, or hexafluorobenzene and filtered. The solvent is then evaporated under reduced pressure to yield a mixture comprised of cyclofluoroalkylated fullerene compounds of formula (I). Addition of an organic or haloorganic solvent such as hexane allows for collection of the product by filtration if it is insoluble, or cooling to $-78°$ C. will precipitate the product which can be then be collected.

Mixtures comprising cyclofluoroalkylated fullerene compounds of this invention are useful as lubricants or as additives to lubricants; in fluorocarbon- and/or chlorofluorocarbon-based cooling systems; in adhesives for fluorocarbon-based polymers; in gas separation membranes.

Unlike most fullerenes known in the art, the mixtures of this invention are surprisingly soluble in a variety of organic liquids, particularly halocarbon liquids, such as chlorofluorocarbons, e.g., 1, 1,2-trichlorotrifluoroethane, and hexafluorobenzene.

EXAMPLE 1

Preparation of $C_{60}(CF_2CF_2)_wH_z$

A purple solution comprised of 50 mg (0.07 mmole) $C_{60}$ dissolved in 25 ml 1,2,4-trichlorobenzene was charged to a 75 ml stainless steel pressure tube under nitrogen and sealed. After cooling to $-50°$ C. and evacuating, 30 g (0.3 mole) tetrafluoroethylene was admitted to the tube. The reaction mixture was heated with shaking to $200°$ C. and maintained for 18 hr during which time the pressure dropped from a maximum of $12.69 \times 10^6$ Pascals to $4.5 \times 10^6$ Pascals. After cooling to room temperature, the pressure was slowly bled off to yield a reddish-brown solution. The 1,2,4-trichlorobenzene was distilled off to dryness under reduced pressure. The residue was taken up in a total of 20-30 mL of hexane. Cooling this hexane solution to $-78°$ C. caused the precipitation of a brown solid. This was isolated by cold filtration ($-78°$ C.) to yield 0.042 g of a brown powder. Removal of hexane from the filtrate yielded 0.044 g more of a brown product. Combined yield: 0.086 g. The product is very soluble in 1,1,2-trichlorotrifluoroethane, hexafluorobenzene, tetrahydrofuran, or hexane. The product is identified by negative ion chemical ionization mass spectroscopy and $^{19}F$ Nuclear Magnetic Resonance spectroscopy as the mixture $C_{60}(CF_2CF_2)_wH_z$, with $w=1-15$ and $z=0$ or 2, the major components being $w=8-9$ and $z=0$.

EXAMPLE 2

Preparation of $C_{60}(CF_2CF_2)_w(C_4F_9)_xH_z$

A solution comprised of 50 mg (0.07 mmole) $C_{60}$ and 2 g (5.8 mmole) 1-iodoheptafluorobutane dissolved in 25 ml 1,2,4-trichlorobenzene was charged to a 75 ml stainless steel pressure tube under nitrogen and sealed. After cooling to $-50°$ C. and evacuating, 10 g (100 mmole) tetrafluoroethylene was admitted to the tube. The reaction mixture was heated with shaking to $180°$ C. and maintained for 18 hr during which time the pressure dropped from a maximum of $4.75 \times 10^6$ Pascals to $2.94 \times 10^6$ Pascals. After cooling to room temperature, the pressure was slowly bled off. The light brown product was isolated by filtration to yield 0.084 g of solid. The product is very soluble in 1,1,2-trichlorotrifluoroethane, hexafluorobenzene, tetrahydrofuran, or hexane. The product is identified by negative ion chemical ionization mass spectroscopy as the mixture $C_{60}(CF_2CF_2)_w(C_4F_9)_xH_z$, with $w=1-17$, $x=0-1$ and $z=0-2$. The distribution of products is bimodal with peaks at $w=5-6$, $x=0$, $z=0$ and $w=11-12$, $x=1$, $z=1$.

EXAMPLE 3

Preparation of $C_{60}(CF_2CF_2)_w(C_2F_5)_xH_z$

A solution comprised of 5 mg $C_{60}(CF_2CF_2)_xH_z$, from Example 1, dissolved in 0.5 ml 1,1,2-trichlorotrifluoroethane was charged to a 5 ml glass tube. After flushing with nitrogen, 0.03 ml of a degassed solution comprised of 6% by weight of perfluoropropionyl peroxide in 1,1,2-trichlorotrifluoroethane was charged to the tube and sealed. The reaction mixture was slowly heated to $70°$ C. in the cavity of an electron spin resonance (ESR) spectrometer until the ESR signal stopped growing. An additional 0.03 ml of a degassed solution comprised of 6% by weight of perfluoropropionyl peroxide in 1,1,2-trichlorotrifluoroethane was added to the reaction under nitrogen and the heating process repeated as above. The 1,1,2-trichlorotrifluoroethane was evaporated to concentrate the sample to a small volume of dark red-brown solution. Electron capture mass spectrometry indicated the formation of the mixture $C_{60}(CF_2CF_2)_w(C_2F_5)_xH_z$ with $w=5-8$, $x=1-8$ and $z=0-2$. The distribution of products peaked at $w=6$, $x=5$, $z=0$.

EXAMPLE 4

Preparation of $C_{60}(CF_2CFCF_3)_w$

A solution comprised of 50 mg (0.07 mmole) $C_{60}$ dissolved in 40 ml 1,2,4-trichlorobenzene was charged to a 230 ml stainless steel pressure tube under nitrogen and sealed. After cooling to $-50°$ C. and evacuating, 45 g (0.3 mole) hexafluoropropene was admitted to the tube. The reaction mixture was heated with shaking to $350°$ C. and maintained for 18 hr during which time the pressure dropped from a maximum of $8.48 \times 10^6$ Pascals to $5.92 \times 10^6$ Pascals. After cooling to room temperature, the pressure was slowly bled off to yield two-phase mixture consisting of a lower clear layer of perfluoro-1,2-dimethyl cyclobutane and a reddish-brown upper layer of 1,2,4-trichlorobenzene. The organic solvents were distilled off to dryness under reduced pressure to yield a dark reddish-brown product. The solid residue was dissolved in 100 ml 1,1,2-trichlorotrifluoroethane and filtered through a 0.5 mm filter and evaporated to dryness. The residue was dissolved in hexafluorobenzene, and transferred to an oil sublimation apparatus. Heating to $120°-130°$ C. under high vacuum for 12 h removed a pale yellow oil. The residue in the bottom of the oil sublimer was washed with a total of 20 mL of hexane yielding 97 mg of a sticky dark orange-brown solid. The product is identified by negative ion chemical ionization mass spectroscopy and $^{19}F$ Nuclear Magnetic Resonance spectroscopy as the mixture $C_{60}(CF_2CFCF_3)_w$ with $w=1-3$; the major component being $w=2$.

EXAMPLE 5

Preparation of $C_{60}(CF_2CFOCF_3)_wH_z$

A solution comprised of 50 mg (0.07 mmole) $C_{60}$ dissolved in 20 ml 1,2,4-trichlorobenzene was charged to a 75 ml stainless steel pressure tube under nitrogen and sealed. After cooling to $-50°$ C. and evacuating, 30 g (0.18 mole) perfluoromethylvinyl ether was admitted to the tube. The reaction mixture was heated with shaking to 200° C. and maintained for 18 hr during which time the pressure dropped from a maximum of $7.5 \times 10^6$ Pascals to $7.06 \times 10^6$ Pascals. After cooling to room temperature, the pressure was slowly bled off to yield a dark-colored solution. The solution was transferred to a flask. The tube was rinsed with small portions of 1,1,2-trichlorotrifluoroethane until the rinses were colorless. The rinses were combined with the reaction mixture and all volatile components were distilled off to dryness under reduced pressure to yield a dark reddish-brown product. The solid residue was dissolved in 40 ml 1,1,2-trichlorotrifluoroethane and filtered through a 0.5 mm filter and evaporated to dryness yielding 107 mg of a dark orange-brown solid. The product is identified by negative ion chemical ionization mass spectroscopy and $^{19}F$ Nuclear Magnetic Resonance spectroscopy as the mixture $C_{60}(CF_2CFOCF_3)_wH_z$ with $w=1–10$ and $z=0–2$. The distribution of products peaks at $w=2–4$ and $z=0$.

EXAMPLE 6

Preparation of $C_{60}/C_{70}(CF_2CF_2)_wH_z$

A saturated solution comprised of 1 g (1.2–1.4 mmole) $C_{60}/C_{70}$ extract slurried in 100 ml 1,2,4-trichlorobenzene was charged to a 400 ml stainless steel pressure tube under nitrogen and sealed. After cooling to −50° C. and evacuating, 50 g (0.5 mole) tetrafluoroethylene was admitted to the tube. The reaction mixture was heated with shaking to 150° C. and maintained for 18 hr during which time the pressure dropped from a maximum of $4.66 \times 10^6$ Pascals to $3.1 \times 10^6$ Pascals. After cooling to room temperature, the pressure was slowly bled off to yield a dark-colored solution. The tube was rinsed with small portions of 1,1,2-trichlorotrifluoroethane until the rinses were colorless. The rinses were combined with the reaction mixture and all volatile components were distilled off to dryness under reduced pressure to yield a dark reddish-brown product. The solid residue was transferred to a soxhlet extraction apparatus and extracted with 1,1,2-trichlorotrifluoroethane for 18 hr. The dark extract was evaporated to dryness yielding 1.53 g of a dark orange-brown solid. The product is identified by negative ion chemical ionization mass spectroscopy and $^{19}F$ Nuclear Magnetic Resonance spectroscopy as the mixture $C_{60}/C_{70}(CF_2CF_2)_wH_z$ with $w=1–11$ and $z=0–2$. The distribution of products peaks at $w=5–7$ and $z=0$.

EXAMPLE 7

Preparation of $C_{60}(CF_2CFCl)_wH_z$

A solution comprised of 50 mg (0.07 mmole) $C_{60}$ dissolved in 20 ml 1,2,4-trichlorobenzene was charged to a 75 ml stainless steel pressure tube under nitrogen and sealed. After cooling to −50° C. and evacuating, 30 g (0.26 mole) chlorotrifluoroethylene was admitted to the tube. The reaction mixture was heated with shaking to 175° C. and maintained for 18 hr during which time the pressure dropped from a maximum of $2.13 \times 10^6$ Pascals to $1.57 \times 10^6$ Pascals. After cooling to room temperature, the pressure was slowly bled off to yield a dark-colored solution. The solution was transferred to a flask. The tube was rinsed with small portions of tetrahydrofuran until the rinses were colorless. The rinses were combined with the reaction mixture and all volatile components were distilled off to dryness under reduced pressure to yield a dark reddish-brown product. The solid residue was dissolved in 40 ml tetrahydrofuran and filtered through a 0.5 mm filter and evaporated to dryness yielding 121 mg of a dark orange-brown solid. The product is identified by negative ion chemical ionization mass spectroscopy and $^{19}F$ Nuclear Magnetic Resonance spectroscopy as the mixture $C_{60}(CF_2CFCl)_wH_z$ with $w=1–10$ and $z=0–2$. The distribution of products peaks at $w=3–4$ and $z=0$.

EXAMPLE 8

Preparation of $C_{60}(CF_2CCl_2)_w$

A solution comprised of 50 mg (0.07 mmole) $C_{60}$ dissolved in 20 ml 1,2-dichlorobenzene was charged to a 75 ml stainless steel pressure tube under nitrogen and sealed. After cooling to −50° C. and evacuating, 25 g (0.19 mole) dichlorodifluoroethylene was admitted to the tube. The reaction mixture was heated with shaking to 200° C. and maintained for 18 hr during which time the pressure dropped from a maximum of $1.95 \times 10^6$ Pascals to $0.81 \times 10^6$ Pascals. After cooling to room temperature, the pressure was slowly bled off to yield a dark-colored solution. The solution was transferred to a flask. The tube was rinsed with small portions of tetrahydrofuran until the rinses were colorless. The rinses were combined with the reaction mixture and all volatile components were distilled off to dryness under reduced pressure to yield a dark reddish-brown product. The solid residue was dissolved in 40 ml tetrahydrofuran and filtered through a 0.5 mm filter and evaporated to dryness yielding 0.57 g of a dark orange-brown solid. The product is identified by negative ion chemical ionization mass spectroscopy and $^{19}F$ Nuclear Magnetic Resonance spectroscopy as the mixture $C_{60}(CF_2CCl_2)_w$ with $w=1–6$. The distribution of products peaks at $w=1–3$.

We claim:

1. A mixture of cyclofluoroalkylated fullerene compounds of formula (I)

$$(C_{60+2n})(CF_2CR^1R^2)_wR^3{}_xR^4{}_yR^5{}_z \qquad I$$

wherein:
$R^1$ and $R^2$ are independently H, F, Cl, Br, CN, a branched or straight chain alkyl, alkylether, alkoxy, alkoxyether, fluoro-alkyl, fluoroalkylether, fluoroalkoxy, fluoroalkoxyether, aryl, aryloxy, fluoro-aryl, or fluoroaryloxy group; optionally substituted with one or more H, Cl, Br, carbinol, carboxylic acid ester, carboxylic acid halide, sulfonyl fluoride, or carbonitrile;

$R^3$ is F or a branched or straight chain fluoroalkyl or fluoroalkylether group;

$R^4$ is a branched or straight chain hydrocarbon alkyl or alkyl ether or aromatic hydrocarbon;

$R^5$ is independently one or more selected from H, F and Cl;

n is an integer from 0 to about 470;

w is an integer from 1 to $16+(n/2)$ for n=an even integer, or from 1 to $16+((n+1)/2)$ for n=an odd integer;

x is an integer from 0 to about $24+n$;

y is an integer from 0 to about $24+n$;

z is an integer from 0 to about $35+n$.

2. The mixture as recited in claim 1, wherein n is an integer from 0 to 5; $R^1$ and $R^2$ are independently H, F, Cl or CN; $R^3$ is a perfluoroalkyl or perfluoroalkylether;

$R^4$ is a hydrocarbon alkyl or alkyl ether; $R^5$ is H; x, y and z are 0 to 3+n; and w is 1 to 15.

3. The mixture as recited in claim 2, wherein n is 0 to 5, $R^5$ is H and z is 0 to 2.

4. The mixture as recited in claim 3, wherein $R^1$ is F and $R^2$ is F.

5. The mixture as recited in claim 3, wherein $R^1$ is F and $R^2$ is $OCF_3$.

6. The mixture as recited in claim 3, wherein $R^1$ is F and $R^2$ is $CF_3$.

7. The mixture as recited in claim 3, wherein $R^1$ is F and $R^2$ is Cl.

* * * * *